United States Patent [19]

Miike et al.

[11] 4,384,042

[45] May 17, 1983

[54] METHOD AND TEST COMPOSITION FOR DETERMINATION OF HYDROGEN PEROXIDE

[75] Inventors: Akira Miike; Yoshiaki Shimizu, both of Shizuoka; Toshio Tatano, Numazu; Katsuyuki Watanabe, Higashimurayama, all of Japan

[73] Assignee: Kyowa Hakko Kogyo Co., Ltd., Tokyo, Japan

[21] Appl. No.: 288,123

[22] Filed: Jul. 29, 1981

[30] Foreign Application Priority Data

Jul. 30, 1980 [JP] Japan ................... 55-103665

[51] Int. Cl.$^3$ .................. C12Q 1/26; C12Q 1/28; C12Q 1/44; C12Q 1/48; C12Q 1/54; C12Q 1/60; C12Q 1/62

[52] U.S. Cl. ...................... 435/25; 435/11; 435/14; 435/15; 435/19; 435/10; 435/28; 435/805; 435/810

[58] Field of Search ............ 435/10, 11, 14, 15, 435/18, 19, 25, 28, 805, 810

[56] References Cited

U.S. PATENT DOCUMENTS

| | | | |
|---|---|---|---|
| 3,654,179 | 4/1972 | Bauer | 435/28 |
| 3,791,988 | 2/1974 | Dieter et al. | 435/14 |
| 3,947,377 | 3/1976 | Werner et al. | 435/14 |
| 3,975,398 | 8/1976 | Werner et al. | 435/14 |
| 4,260,679 | 4/1981 | Tsuda et al. | 435/10 |

FOREIGN PATENT DOCUMENTS

| | | |
|---|---|---|
| 2110342 | 9/1972 | Fed. Rep. of Germany . |
| 1299845 | 12/1972 | United Kingdom . |
| 1400897 | 7/1975 | United Kingdom . |
| 1473945 | 5/1977 | United Kingdom . |
| 2002517 | 2/1979 | United Kingdom . |

OTHER PUBLICATIONS

Chem. Abstracts, vol. 80, No. 12, Mar. 25, 1974, p. 482, abstract 66505b.

Chem. Abstracts, vol. 89, No. 14, Oct. 2, 1978, p. 888, abstract 122422x.

*Primary Examiner*—Esther M. Kepplinger
*Attorney, Agent, or Firm*—Fitzpatrick, Cella, Harper & Scinto

[57] ABSTRACT

Disclosed is a method for the colorimetric determination of hydrogen peroxide in a sample by reacting a particular chromogen with the hydrogen peroxide in the presence of peroxidase and measuring the absorbancy of the reaction solution in the visible ray region. Also disclosed is a test composition for carrying out the determination.

14 Claims, 19 Drawing Figures

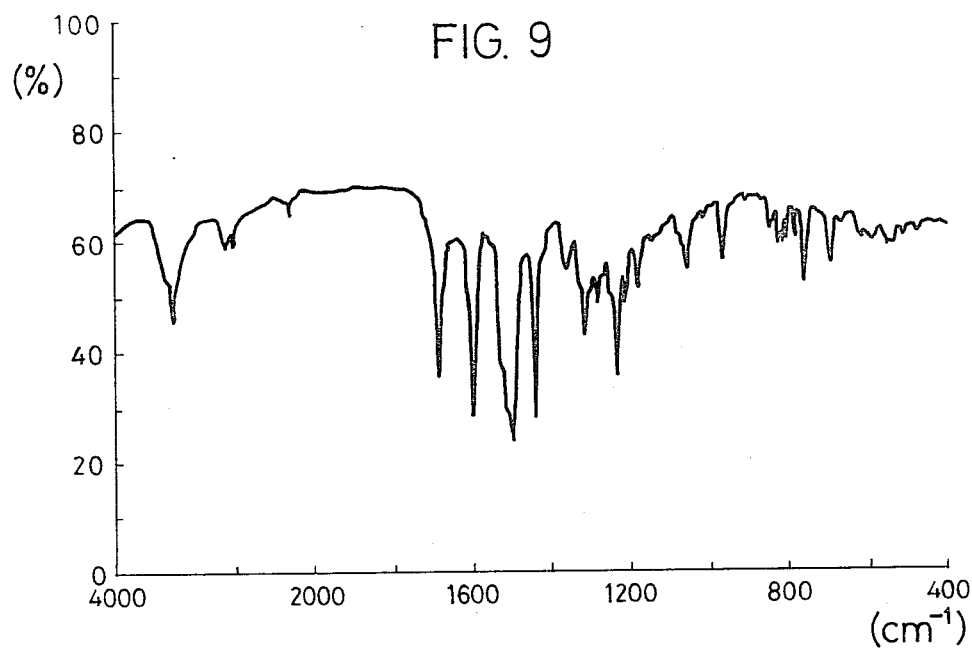
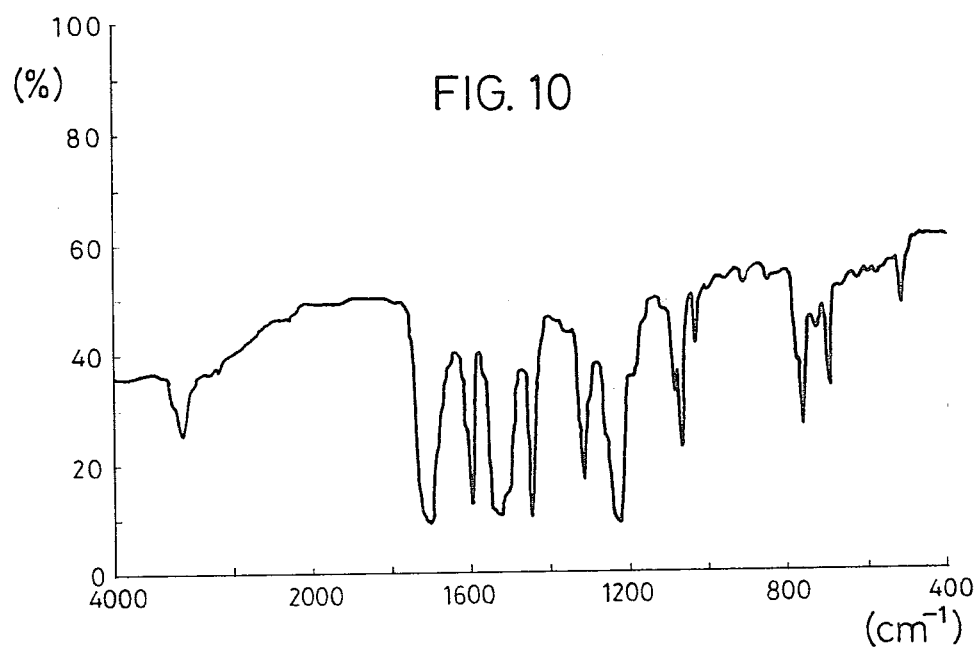

METHOD AND TEST COMPOSITION FOR DETERMINATION OF HYDROGEN PEROXIDE

BACKGROUND OF THE INVENTION

The present invention relates to a method and test composition for the determination of hydrogen peroxide, and more particularly, to a method for the determination of hydrogen peroxide by reacting hydrogen peroxide with a novel chromogen as a hydrogen donor in the presence of peroxidase and determining the degree of pigment formed. The invention also pertains to a test composition suitable for carrying out such determination.

Heretofore, the determination of a substrate was generally carried out by oxidizing the substrate by the action of oxidase and determining the formed hydrogen peroxide. For example, uric acid is oxidized by uricase and cholesterol is oxidized by cholesterol oxidase to form hydrogen peroxide. The hydrogen peroxide is then determined by reacting the hydrogen peroxide with a chromogen in the presence of peroxidase to form a pigment and measuring the absorbancy of the reaction solution colored by the formation of the pigment in the visible ray region. In such processes, 4-aminoantipyrine (hereinafter referred to as "4AA") and phenol, 4AA and N,N-dimethylaniline, 4AA and N-ethyl-N-($\beta$-hydroxyethyl)-m-toluidine, 3-methylbenzothiazolin hydrazone and N,N-diethylaniline, and the like were generally used as the chromogen.

While the known methods were acceptable, there is a need for chromogens which are superior in sensitivity and stability of color and which are not affected by the components in vivo such as hemoglobin, bilirubin and glutathione.

SUMMARY OF THE INVENTION

It has now been found that a compound represented by either of the following formula (I) or (II) is excellent as a chromogen.

Formula (I):

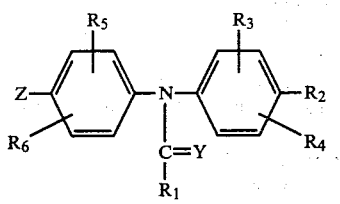

Formula (II):

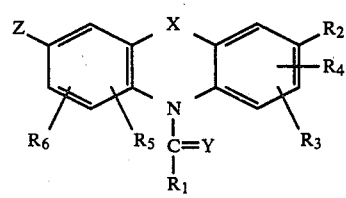

In the above formulae, Z represents hydroxyl, amino or substituted amino, Y represents an oxygen atom or a sulfur atom, $R_1$ represents hydrogen, alkyl, alkenyl, aryl, amino or mono-substituted amino, $R_2$ represents hydrogen, hydroxyl, alkyl, aryl, alkenyl, amino, alkylamino or alkoxy, $R_3$, $R_4$, $R_5$ and $R_6$ represent hydrogen, alkyl, alkenyl, acyl, aryl, halogen, nitro, sulfo, carboxyl, hydroxyl, hydroxyalkyl or alkoxy, $R_3$ and $R_4$ or $R_5$ and $R_6$ may form alkenylene, X represents —S—, —O—,

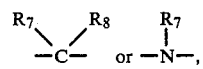

$R_7$ and $R_8$ represent hydrogen, alkyl, alkenyl or aryl.

In the definition of Z, substituted amino means mono- or di-substituted amino and the substituents mean alkyl, alkenyl, aryl, hydroxyalkyl or acylalkyl.

In the definition of $R_1$, substituent of mono-substituted amino includes alkyl, cycloalkyl, substituted alkyl, alkenyl and aryl.

Alkenylene include alkenylene having 3–4 carbon atoms such as —CH=CH—CH=CH—, —CH=CH—CH$_2$—, etc.

As used herein, alkyl includes alkyl having 1 to 4 carbon atoms, such as methyl, ethyl, propyl and butyl; alkenyl includes alkenyl having 2 to 5 carbon atoms such as vinyl, propylene and butylene; aryl includes phenyl, benzyl, naphthyl, and substituted phenyl; substituent of substituted phenyl includes alkyl having 1 to 4 carbon atoms, halogen such as chloro atom and bromo atom, amino, alkoxycarbonylamino, alkoxycarbonylaminoalkyl, alkoxy and acyl; substituted phenyl may have 1 to 5 substituents; acyl includes acyl having 2 to 5 carbon atoms such as acetyl, propionyl and butyryl; halogen includes chloro atom and bromo atom; alkoxy includes alkoxy having 1 to 4 carbon atoms such as methoxy, ethoxy, propoxy and butoxy. In the definition of $R_1$, the substituents of substituted alkyl includes alkoxycarbonylamino, phenyl, substituted phenyl and the substituted phenyl has the same significance as defined above.

These compounds are generally known and are readily prepared by the methods illustrated by the following reaction formulae.

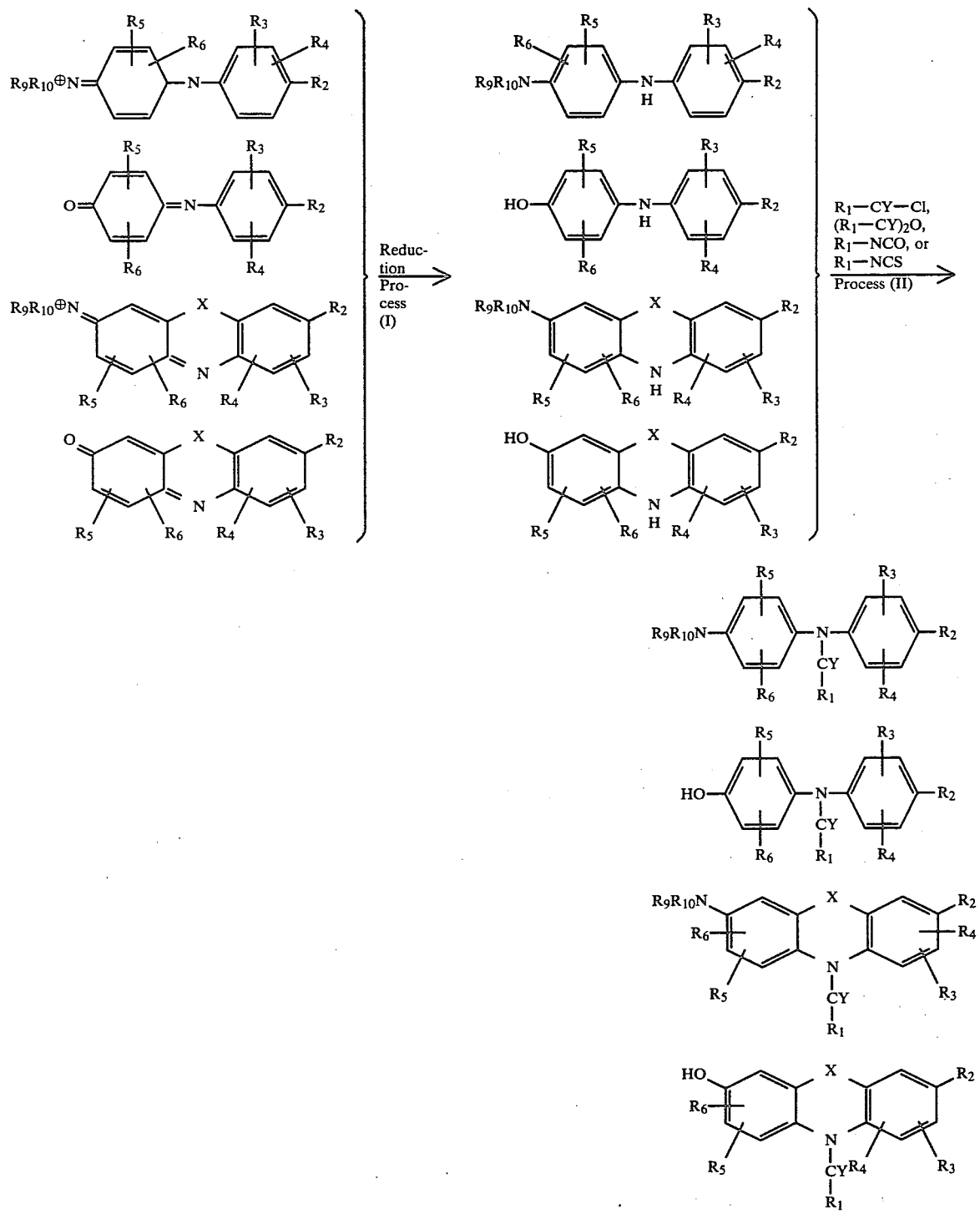

In the foregoing formulae, $R_1$-$R_6$, $R_9$, $R_{10}$, X and Y have the same significance as defined above.

The raw materials are known pigments.

In the Process (I), the raw material is subjected to reduction in the presence of reducing agents such as $NaBH_4$, Fe-HCl. The reduction is carried out in a solvent such as water, methanol, acetone and the like at from room temperature to the boiling point of the used solvent. After the raw materials are decolorized, the reduction product is isolated from the reaction mixture.

To the isolated reduction product or the reaction mixture are added an acylating agent, an alkylthiocarbonylating agent, ester of isocyanic acid, or ester of isothiocyanic acid. The reaction is usually at from room temperature of the boiling point of the solvent used.

The isolation of the desired product from the reaction mixture is carried out by a suitable isolation means in organic synthesis such as extraction, concentration, chromatography, recrystallization, filtration, etc.

BRIEF DESCRIPTION OF THE DRAWINGS

In the accompanying drawings FIGS. 1 to 10 respectively illustrate the infrared absorption spectra of the compounds identified as compounds I-1 to 3 and II-4 to 10 in Table 1 below.

DESCRIPTION OF THE INVENTION

Figure 1:
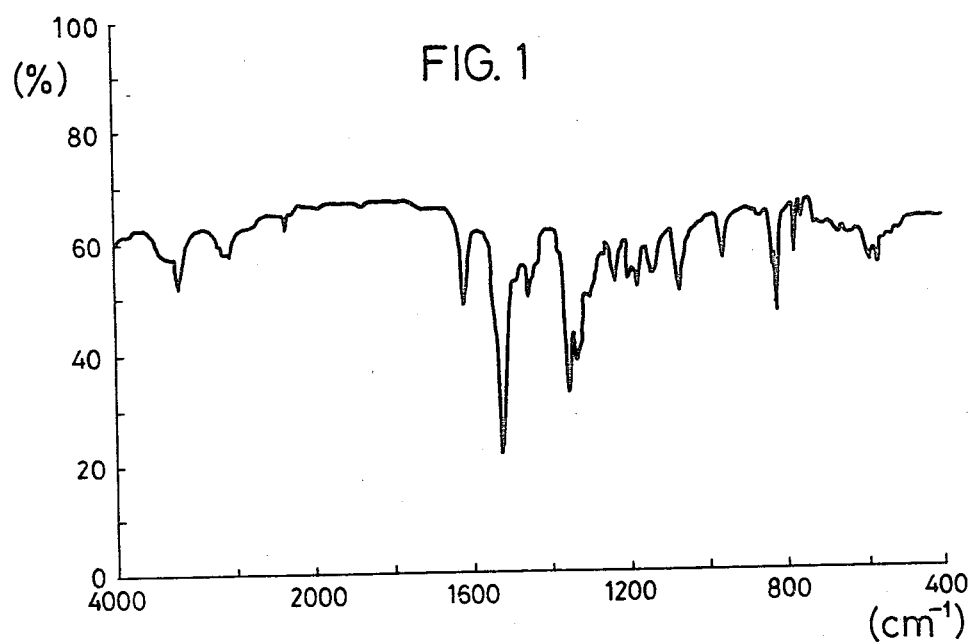
Figure 2:
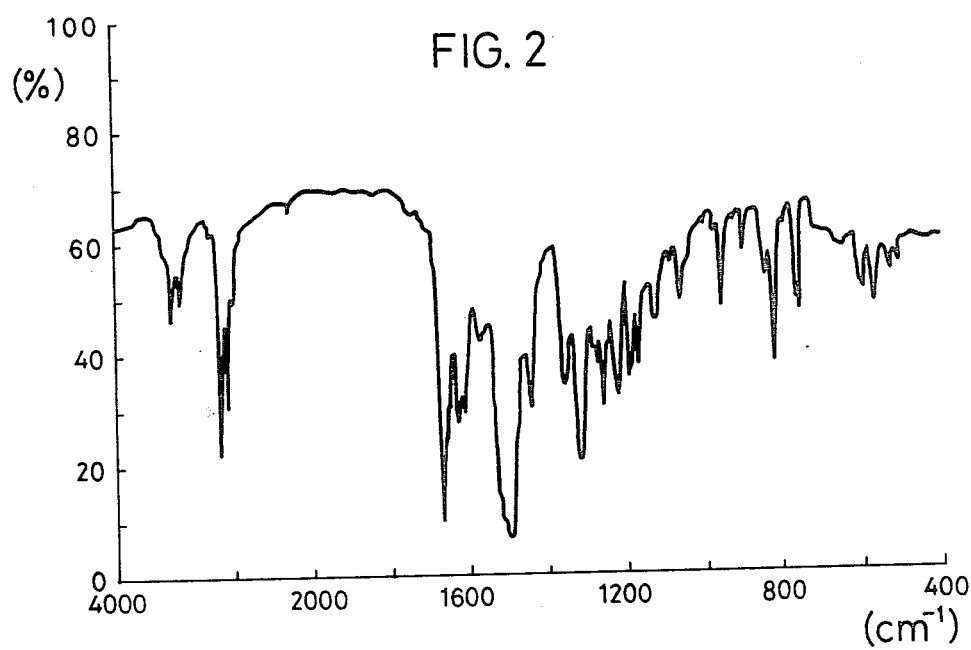
Figure 3:
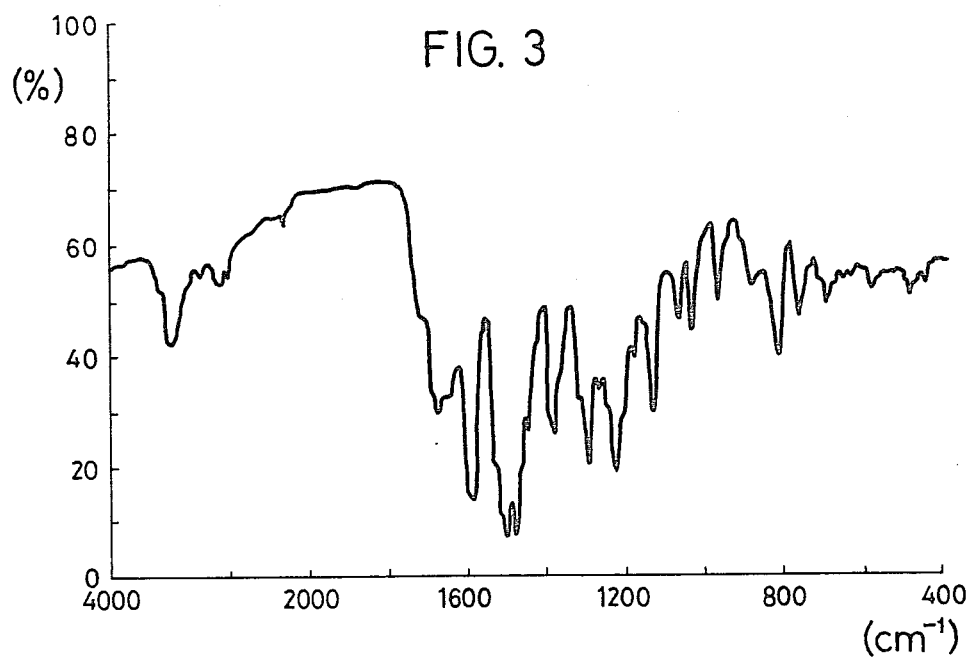
Figure 4:
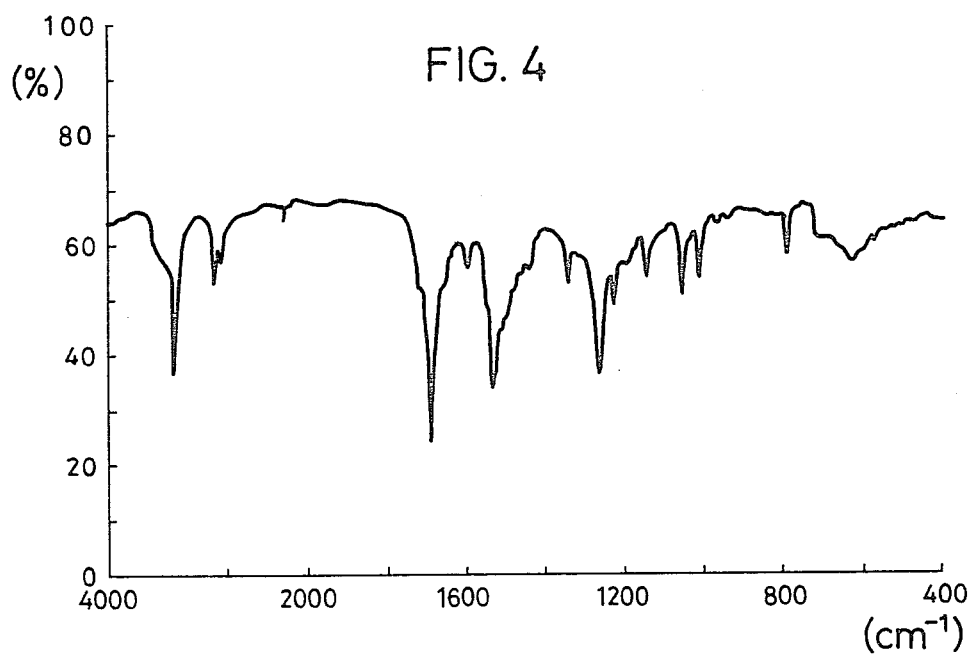
Figure 5:
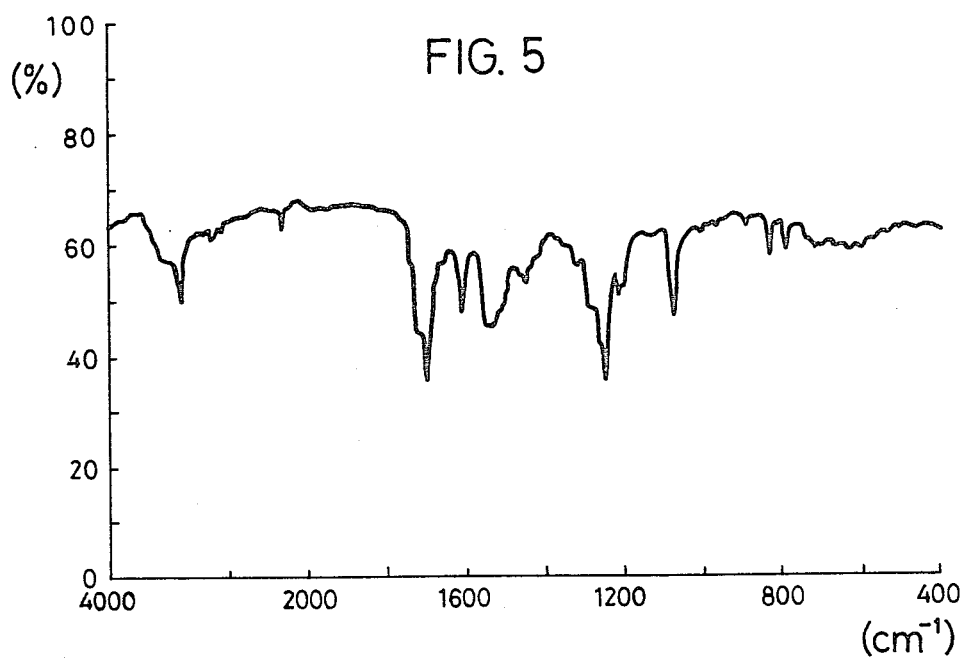
Figure 6:
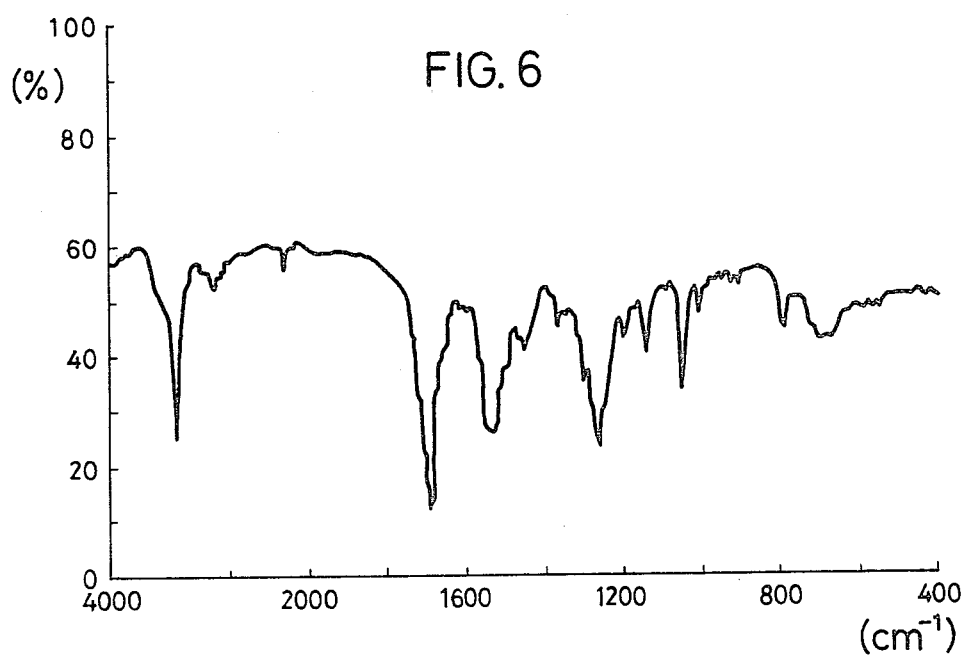
Figure 7:
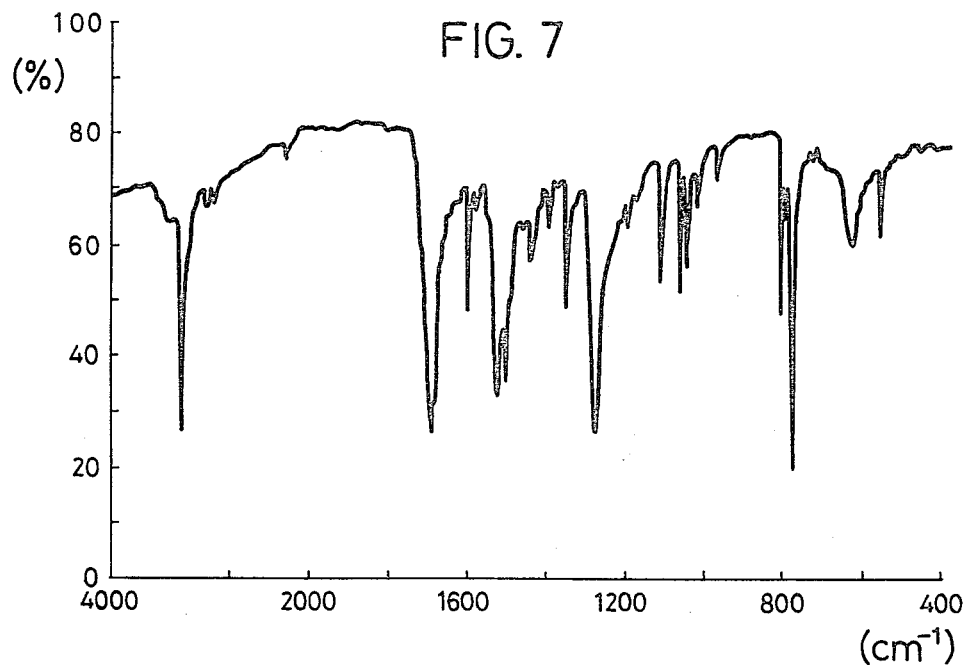
Figure 8:
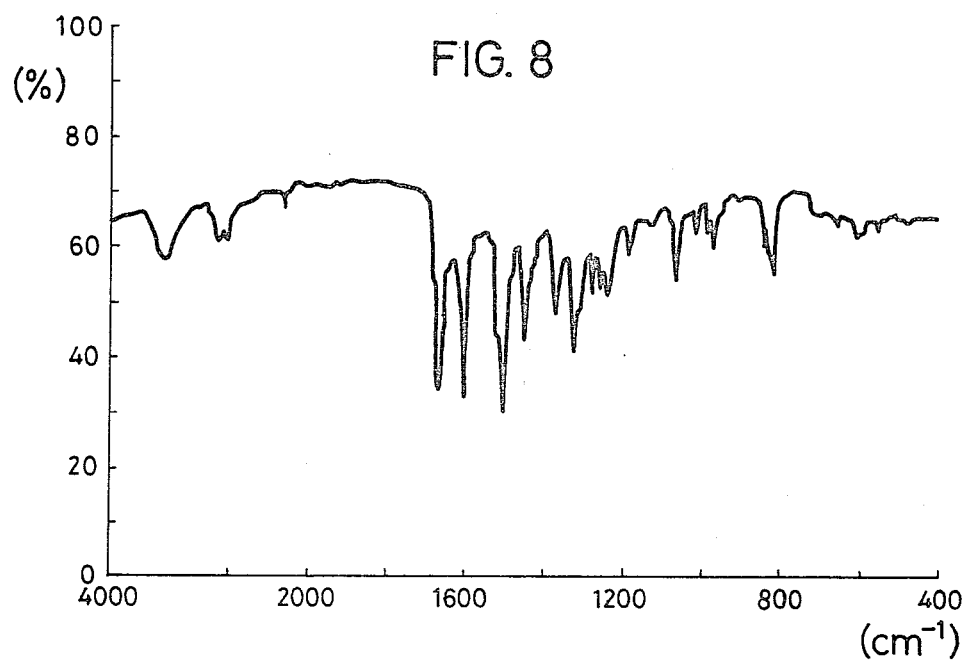
Figure 11:
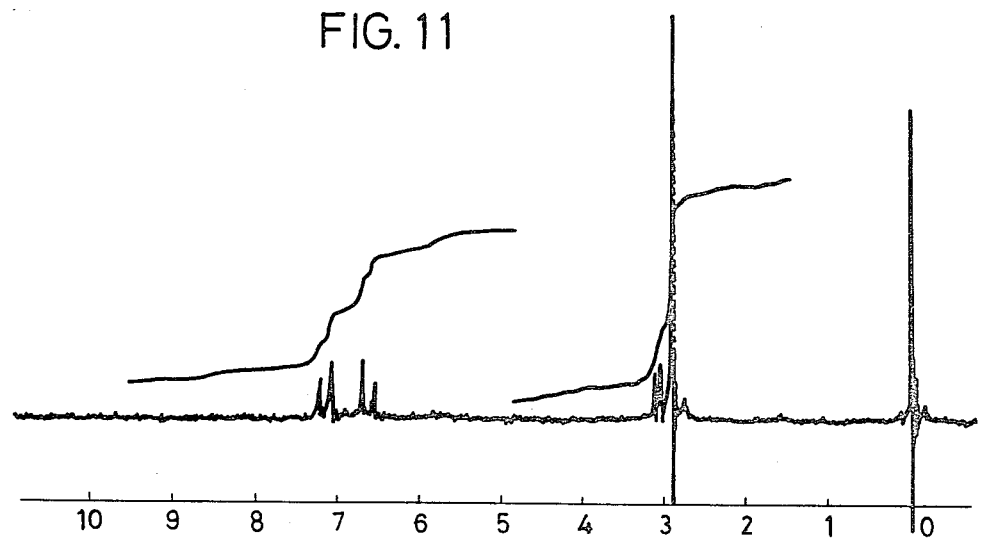
FIGS. 11 to 19 respectively illustrate the NMR spectra in CDCl₃ of compounds I-1 to 2 and II-4 to 10 in Table 1 below.
Figure 12:
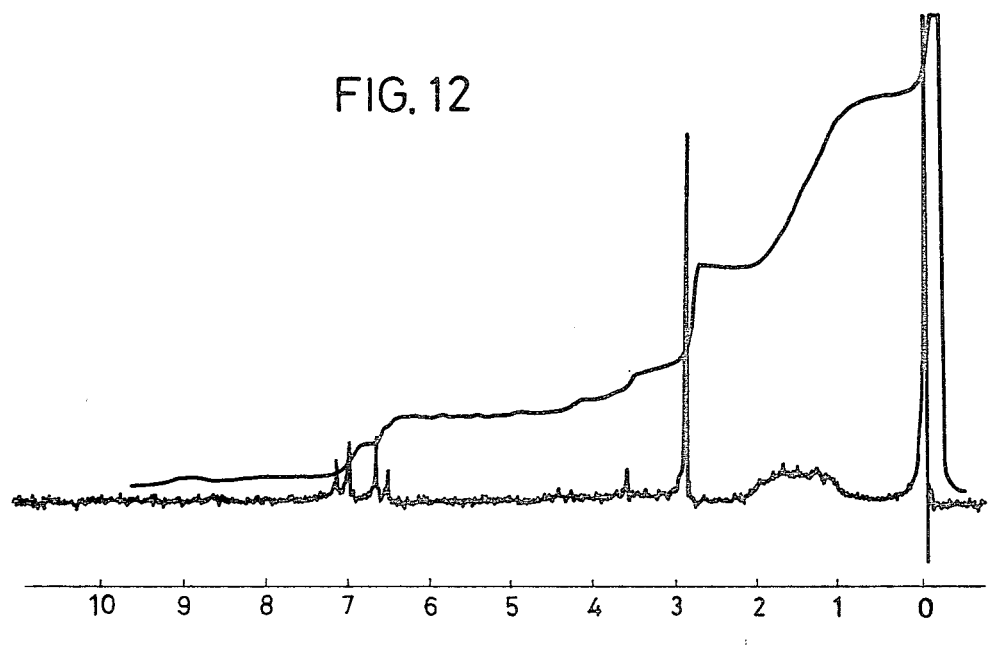
Figure 13:
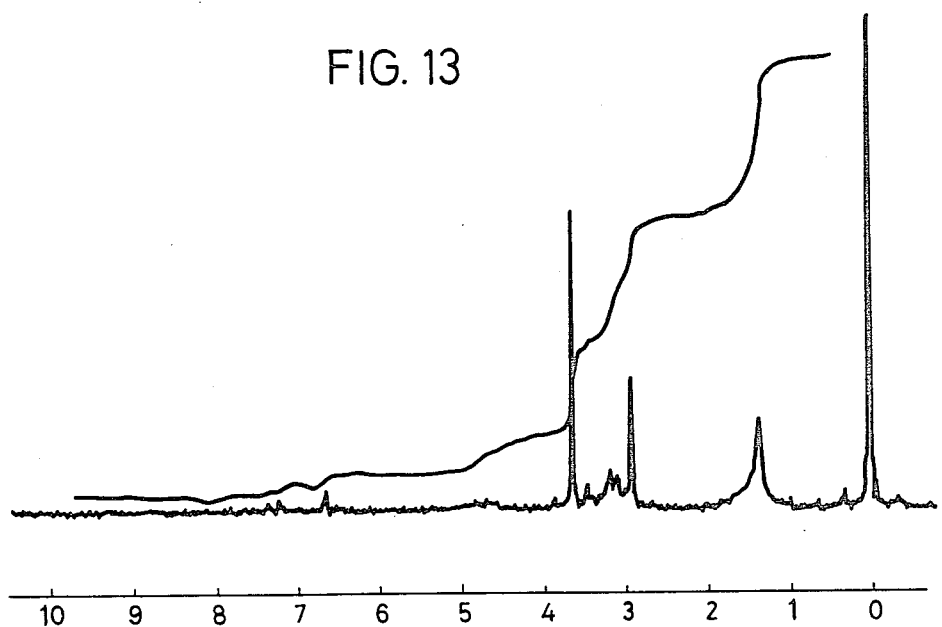
Figure 14:
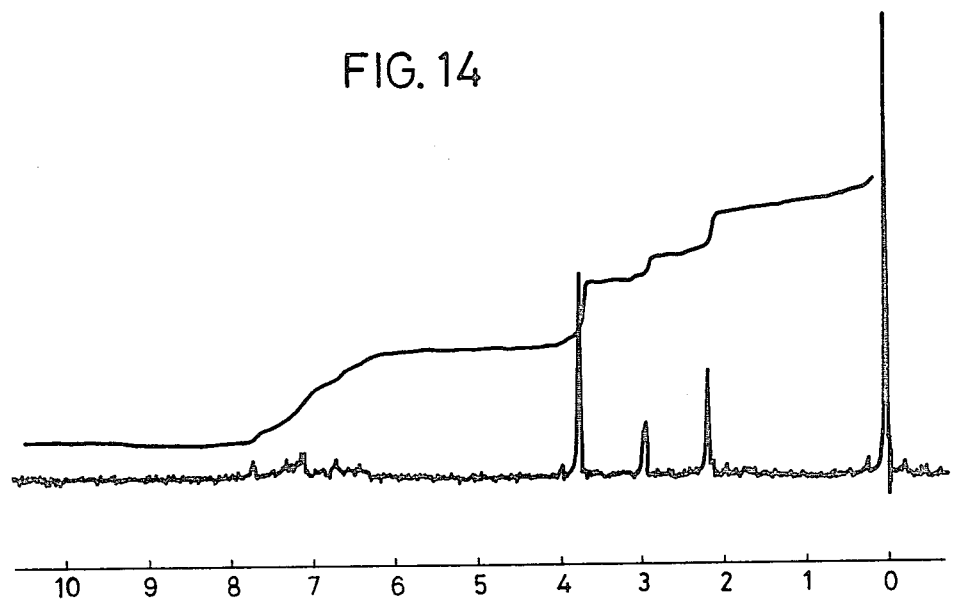
Figure 15:
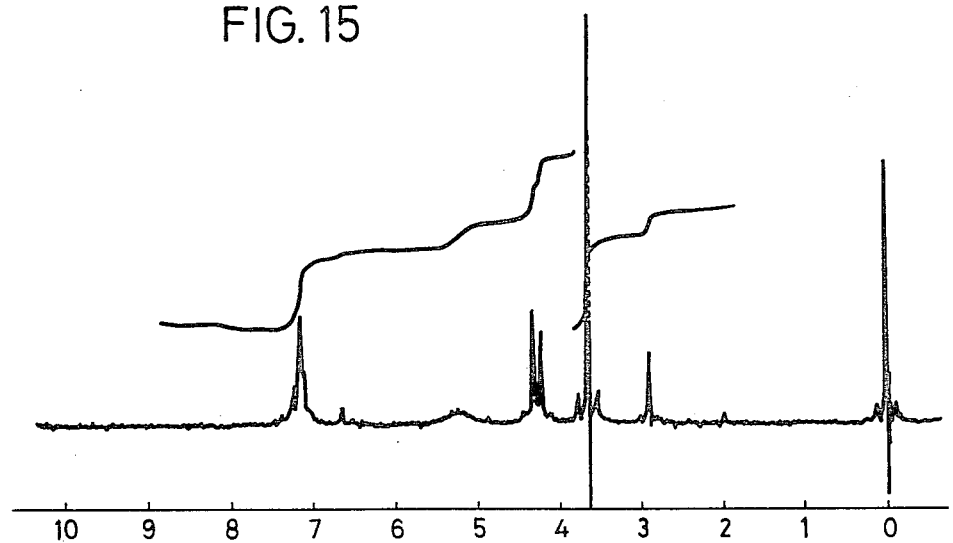
Figure 16:
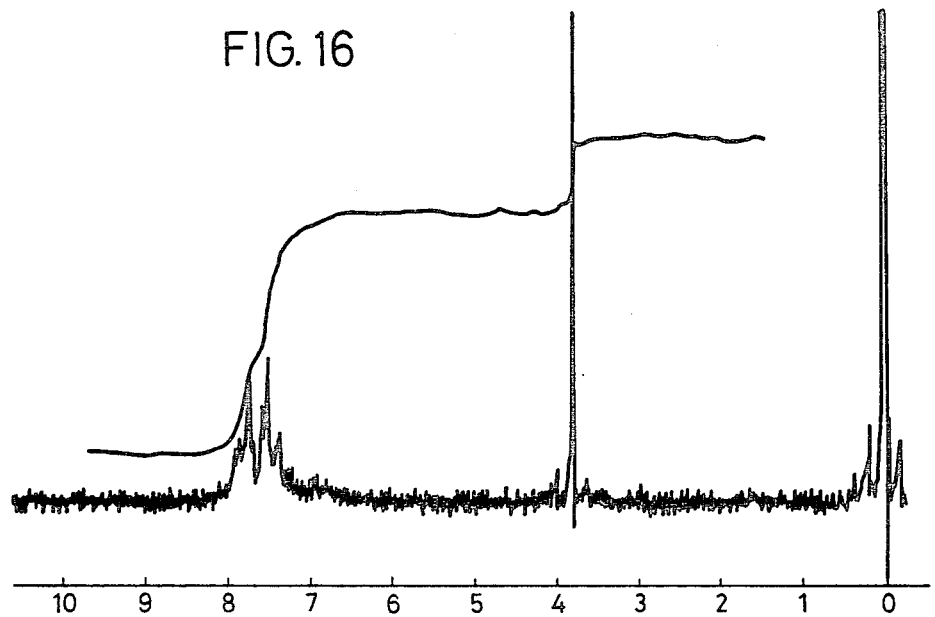
Figure 17:
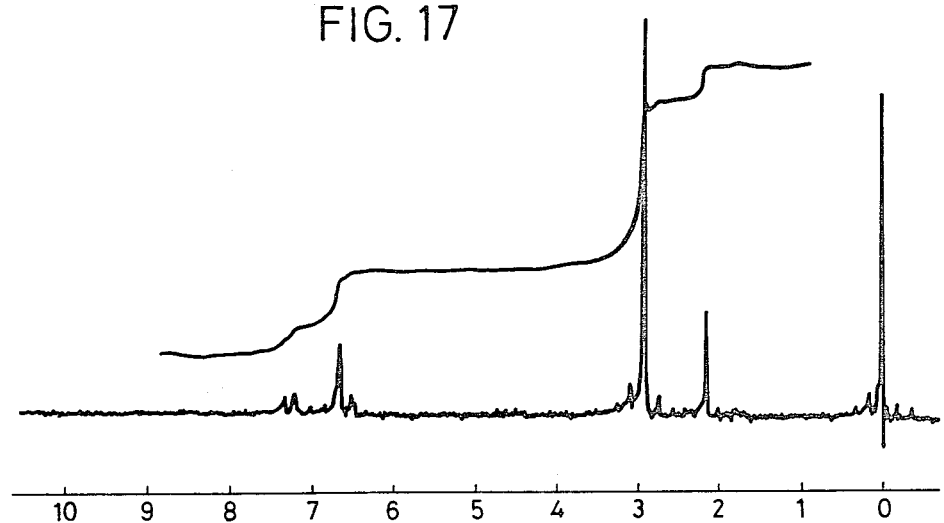

Examples of chromogens used in the present invention are shown in Table 1 below, wherein the symbols "I" or "II" in Table 1 mean a compound of formula (I) or (II) [hereinafter referred to as compound (I) or (II), respectively].

TABLE 1

| Compound No. | Z | X | Y | $R_1$ | $R_2$ | $R_3$ | $R_4$ | $R_5$ | $R_6$ |
|---|---|---|---|---|---|---|---|---|---|
| I-1 | N(CH₃)₂ | — | S | NHCH₃ | N(CH₃)₂ | H | H | H | H |
| I-2 | N(CH₃)₂ | — | O | NH—⟨cyclohexyl⟩ | N(CH₃)₂ | H | H | H | H |
| I-3 | N(CH₃)₂ | — | O | NH—⟨cyclohexyl-Cl,Cl⟩ | N(CH₃)₂ | H | H | H | H |
| II-4 | N(CH₃)₂ | S | O | NH(CH₂)₆NHCOOCH₃ | N(CH₃)₂ | H | H | H | H |
| II-5 | N(CH₃)₂ | S | O | NH—⟨cyclohexyl(CH₃)(NHCOOCH₃)⟩ | N(CH₃)₂ | H | H | H | H |
| II-6 | N(CH₃)₂ | S | O | NHCH₂—⟨cyclohexyl-CH₂NHCOOCH₃⟩ | N(CH₃)₂ | H | H | H | H |
| II-7 | N(CH₃)₂ | S | O | NH—⟨decalinyl⟩ | N(CH₃)₂ | H | H | H | H |
| II-8 | N(CH₃)₂ | S | O | CH₃ | N(CH₃)₂ | H | H | H | H |
| II-9 | N(CH₃)₂ | S | O | NH—⟨cyclohexyl⟩ | N(CH₃)₂ | H | H | H | H |
| II-10 | N(CH₃)₂ | O | O | NH—⟨cyclohexyl⟩ | H | | H | H | A |

A: —CH=CH—CH=CH—

The principle of the present invention is on the basis of the fact that the reaction of hydrogen peroxide with the present chromogen proceeds stoichiometrically to form a pigment and the amount of formed pigment is proportional to the amount of hydrogen peroxide in the sample.

The principle is illustrated as follows.

Cases where Z is amino or substituted amino
POD means peroxidase.

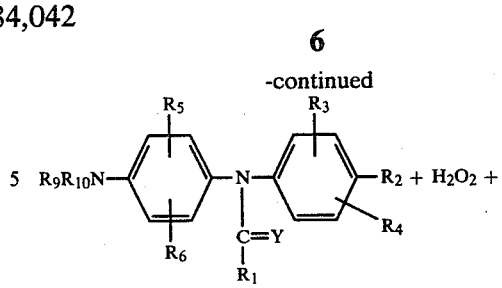

[I-A]

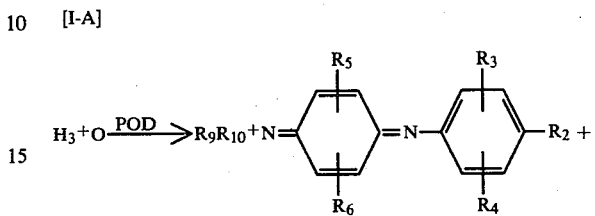

[I-A']

$$R_1-\overset{Y}{\underset{\|}{C}}OH + 2H_2O$$

[II-A]

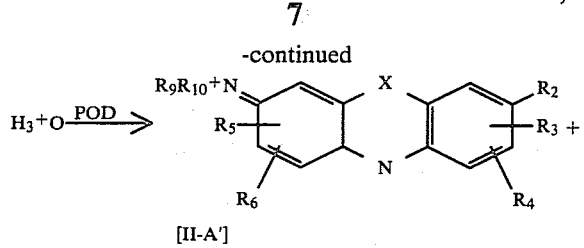

[II-A']

$$R_1-\overset{\overset{Y}{\|}}{C}OH + 2H_2O$$

Cases where Z is OH

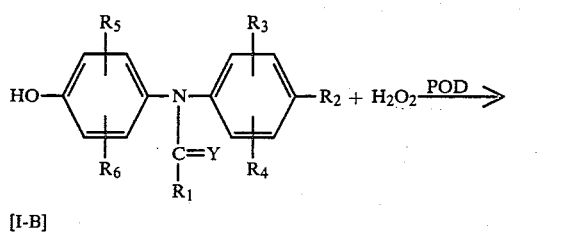

[I-B]

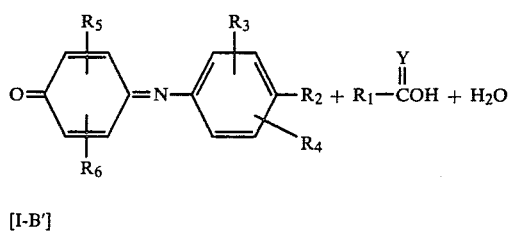

[I-B']

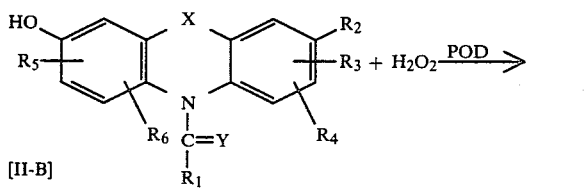

[II-B]

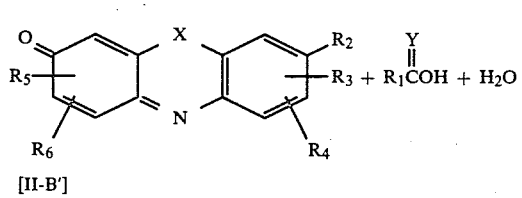

[II-B']

Compounds [I-A'], [I-B'], [II-A'] and [II-B'] formed in the above reactions are known pigments such as Bindschedler's Green, indophenol, Methylene Blue, etc. These pigments are excellent in stability and therefore, are suitable for the determination of hydrogen peroxide by colorimetry of the solution colored by the formation of pigment.

Comparative tests between the compounds indicated in Table 1 and known compounds in respect of the degree of color development and the stability of the color formed in the reaction with hydrogen peroxide are conducted according to the following method.

A test solution containing 0.1 mg/ml of the compounds indicated in Table 1, 10 IU/ml POD and if necessary, 0.1% surfactant in a phosphate buffer solution (pH 6.0) is prepared. To 3 ml of the test solution there is added 20 μl hydrogen peroxide solution and the absorbancy of the colored reaction solution (E) is measured at maximum absorption wave-length (λmax) of the formed pigment.

The blank absorbancy ($E_B$) is measured by repeating the same procedures as described above except using water instead of hydrogen peroxide solution.

The degree of the color development (E-$E_B$) of the test compound is calculated defining the degree of color development (E-$E_B$)' of 4AA-phenol ($A_1$) as 100.

For comparison, 4AA-dimethylaniline ($A_2$) and 4AA-diethylaniline ($A_3$) are used as the chromogen.

The stability of color is determined as follows. The value of (E-$E_B$) immediately after the reaction is discontinued (in about 30 minutes) is measured. Then the reaction solution is further incubated at 37° C. for 4 hours and then (E-$E_B$) is calculated. The symbol "±" means that the decrease of the value of E-$E_B$ is 0–5% by the further incubation and "+" means that the decrease is 5–10%.

The results are shown in Table 2.

TABLE 2

| Chromogen | λ max(nm) | Degree of color | Stability |
|---|---|---|---|
| $A_1$ | 505 | 100 | ± |
| $A_2$ | 550 | 160 | + |
| $A_3$ | 550 | 180 | + |
| I-1 | 728 | 1109 | ± |
| I-2 | 728 | 1022 | ± |
| I-3 | 728 | 981 | ± |
| II-4 | 665 | 1016 | ± |
| II-5 | 665 | 1077 | ± |
| II-6 | 665 | 1054 | ± |
| II-7 | 665 | 962 | ± |
| II-8 | 665 | 1183 | ± |
| II-9 | 665 | 1140 | ± |
| II-10 | 568 | 947 | ± |

When compound (I) or (II) is used as the chromogen, the maximum absorption wavelength in the visible ray region of the pigment is larger than that of hemoglobin contained in serum, which is around 400 nm, and therefore the absorbancy by the present method is not affected by hemoglobin.

Moreover, when there is a turbid sample such as serum containing a large amount of lipids, the turbidity causes an error on the absorbancy. The change of the absorbancy caused by the turbidity increases as the wavelength decreases. Thus, compound (I) or (II) are advantageous because the absorbancy is not affected by the turbidity.

In carrying out the determination of hydrogen peroxide according to the present invention, the compound (I) or (II) and POD are added to the system where hydrogen peroxide is produced (hereinafter referred to as "$H_2O_2$-producing system"). The absorbancy of the reaction solution colored by the formation of pigment is measured in the visible ray region, 400–760 nm. On the other hand, the standard curve showing the relation between the amount of hydrogen peroxide and absorbancy is separately prepared by using a standard hydrogen peroxide solution as the sample. The amount of hydrogen peroxide in the sample is calculated by applying the obtained absorbancy to the standard curve.

The reaction is usually carried out at a temperature of 5°–50° C., preferably 25°–40° C. in a buffer solution having a pH of 2–10 and is completed in several minutes.

The chromogen is used in an equimolar amount with hydrogen peroxide or more, preferably 10–1000 mole equivalents. Peroxidase is used in a concentration of 0.1–1000 IU/ml.

As buffers, phosphate buffer, tris-HCl buffer, succinate buffer, citrate buffer, acetate buffer, etc. may be used in a concentration of 0.005–2 mol/l.

The present method may apply for the determination of reactants in the system where hydrogen peroxide is produced. Particularly, when the system is an enzymatic reaction, both the $H_2O_2$-producing system and the system where pigment is produced [hereinafter referred to as pigment-producing system] proceed at the same time in the same system and therefore, such a method is simple and convenient.

Such enzymatic reaction includes the combination of oxidase and a substrate thereof, examples of which are the combination are uric acid-uricase, cholesterol-cholesterol oxidase, cholesterol ester-cholesterol esterase and cholesterol oxidase, xanthin, hypoxanthin or guanine-xanthin oxidase, phospholipase D-lecitin-choline oxidase, choline-choline oxidase, pyruvic acid-pyruvate oxidase-phosphoric acid, triglyceride-lipoprotein lipase-ATP-glycerinkinase-glycerin-3-phosphate oxidase, fatty acid-coenzyme A-acyl Co A synthetase-acyl Co A oxidase, triglyceride-lipase-glycerol oxidase, glucose-glucose oxidase and galactose-galactose oxidase.

The substrates of these enzymatic reactions are contained in serum, urea, etc. and the determination of the substrates is useful for diagnostic purposes.

The hydrogen peroxide-producing reaction and pigment-producing reaction may be conducted stepwise or preferably, the determination of hydrogen peroxide is performed by adding to the sample the components necessary for the determination of hydrogen peroxide conducting all the reactions in one step and measuring the absorbancy of the reaction solution.

The components comprises oxidase for the substrate to be determined, peroxidase, compound (I) or (II). A buffer solution and surfactant, etc. may be added, if necessary. Of course, if components for oxidizing the substrate in addition to oxidase for the substrate are required, such components must be added to the $H_2O_2$-producing system.

Another aspect of the present invention is to provide a test composition for the determination of hydrogen peroxide which comprises oxidase for the substrate to be determined, the chromogen represented by the formula (I) or (II) and peroxidase. The composition may also contain a buffer reagent as well as surfactants such as polyoxyethylenealkylether, antiseptics such as sodium azide, ascorbate osidase for decomposing ascorbic acid, etc. if necessary. Further the composition may contain components necessary for producing hydrogen peroxide other than oxidase for the substrate.

Certain specific embodiments of the invention are illustrated by the following representative examples.

EXAMPLE 1

In this example, 0.1 M phosphate buffer solution (pH 6.0) containing 10 IU/ml peroxidase, 0.1 IU/ml uricase, 0.1 mg/ml compound II-6 and 0.1% Triton X-100 (trade mark of Rohm and Haas Co., U.S.A. for i-octylphenoxypolyethoxy ethanol) is prepared as a test solution. To 3 ml portions of the test solution there is added 20 μl of the samples indicated in Table 3 and each mixture is incubated for reaction at 37° C. with stirring for 10 minutes.

The absorbancy of each reaction solution at 665 nm is then measured.

For comparison, the same procedures as described above are repeated except that 4AA-diethylaniline is used instead of compound II-6 and the absorbancy of the reaction solution at 550 nm is measured. The results are shown in Table 3.

The following samples are referred to as $S_{1-4}$.
$S_1$: 10 mg/dl uric acid standard solution
$S_2$: normal human serum
$S_3$: gouty patient serum
$S_4$: deionized water

TABLE 3

| | the present method | | 4AA-diethylaniline | |
|---|---|---|---|---|
| | absorbancy | uric acid (mg/ml) | absorbancy | uric acid (mg/ml) |
| $S_1$ | 0.322 | (10.0) | 0.056 | (10.0) |
| $S_2$ | 0.157 | 4.6 | 0.026 | 4.4 |
| $S_3$ | 0.282 | 8.7 | 0.050 | 8.9 |
| $S_4$ | 0.014 | — | 0.002 | — |

As for the sample $S_2$, both the present method and the method using 4AA-diethylaniline are repeated 10 times to measure the absorbancy. The results are shown in Table 4.

TABLE 4

| | the present method | | 4AA-diethylaniline | |
|---|---|---|---|---|
| | absorbancy | uric acid (mg/dl) | absorbancy | uric acid (mg/dl) |
| 1 | 0.157 | 4.64 | 0.027 | 4.63 |
| 2 | 0.157 | 4.64 | 0.027 | 4.63 |
| 3 | 0.156 | 4.61 | 0.026 | 4.44 |
| 4 | 0.160 | 4.74 | 0.024 | 4.07 |
| 5 | 0.159 | 4.71 | 0.026 | 4.44 |
| 6 | 0.158 | 4.68 | 0.026 | 4.44 |
| 7 | 0.157 | 4.64 | 0.025 | 4.26 |
| 8 | 0.156 | 4.61 | 0.025 | 4.26 |
| 9 | 0.159 | 4.71 | 0.028 | 4.81 |
| 10 | 0.157 | 4.64 | 0.027 | 4.63 |
| the average | 0.157 | 4.66 | 0.026 | 4.46 |
| coefficient of variation | 0.81% | 0.92% | 4.35% | 4.72% |

As is apparent from Table 4, the coefficient of variation in the present method is very small and therefore the present method is excellent in its accuracy.

EXAMPLE 2

In this example, the same procedures as described in Example 1 are repeated except that the chromogens indicated in Table 1 are used instead of compound II-6 and the enzymatic reactions with normal serum are carried out. The absorbancy of each reaction solution is measured at λ max of each chromogen to obtain similar results to that of compound II-6.

EXAMPLE 3

In this example, a reagent solution is prepared by dissolving 10 mg of Compound II-6 in 100 ml of 0.1 M phosphate buffer solution (pH 6.0) containing 15 mg of co-carboxylase, 200 IU of pyruvate oxidase, 0.1 ml of Triton X-100 and 500 IU of peroxidase.

To three test tubes, each containing 3 ml of the reagent solution, there is added (A) 0.05 ml of distilled water (B) 1 mg/dl pyruvic acid standard solution or (C) 0.05 ml of serum and each mixture is incubated at 37° C. for 20 minutes. The absorbancy of each reaction solution is measured at 666 nm and the concentration of pyruvic acid in the serum is determined at 1.04 mg/dl.

EXAMPLE 4

In this example, 100 ml of 0.05 M phosphate buffer solution (pH 6.0) containing 0.1 ml of Triton X-100, 100U of peroxidase 3.3U of acyl Co A synthetase, 1.7U of acyl-Co A oxidase, 33 μmol of Co enzyme A, 133 μmol of ATP, 133 μmol of magnesium chloride and 10 mg of compound II-4 is prepared as the reagent solution.

To 3 ml of the reagent solution there is added 0.02 ml of serum and the mixture is incubated at 37° C. for 20 minutes. The absorbancy of the reaction solution is measured at 666 nm.

On the other hand, a standard curve is obtained by repeating the above procedures using a standard solution of parmitic acid and distilled water as a sample.

The acid content in the serum is calculated at 394 μeq/l.

EXAMPLE 5

In this example, the following reagent solutions are prepared for comparison. Reagent solution (1):

0.1 M phosphate buffer solution (pH 6.0) containing 20 mg/l hydrogen peroxide, 0.1 mg/ml compound II-6 and 0.1% Triton X-100. Reagent solution (2):

The reagent solution having the same composition as that of reagent solution (1) except that 0.1 mg/ml 4-AA and 0.2 mg/ml N,N-diethylaniline is used instead of compound II-6. Reagent solution (3):

A solution containing slight peroxidase activity.

For the determination 3 ml of reagent solution (1) is heated at 37° C. for 10 minutes and then 50 μl of reagent solution (3) is added. One minute after the addition, the absorbancy of the mixture at 665 nm, is measured which is defined as $E_1$. Thereafter the absorbancy, measured 5 minutes after the addition, is defined as $E_5$.

A similar reaction is then carried out using reagent solution (2) to obtain the absorbancies at 550 nm one minute after the addition and 5 minutes after the addition, which are defined as $E_1'$ and $E_5'$, respectively. The result is that the value of $E_5-E_1$ is 6.2 times as much as that of $E_5'-E_1'$. Therefore, it is concluded that the present method is excellent in its sensitivity.

EXAMPLE 6

In this example, 1 g of Methylene Blue (produced by Wako Junyaku Co., Ltd.) is dissolved in 100 ml of water and 1 g of sodium salt of hydrogen borohyderide is added to the solution by portions. The mixture is subjected to reaction at 20° C.

When precipitates are formed and the reaction solution is discolored, 20 ml of chloroform is added and the mixture is vigorously stirred. The chloroform layer is separated off and 1 g of natrium sulfate anhydride is added to the chloroform layer. The mixture is stirred, filtered, dehydrated and desalted. Then 2 ml of phenylisocyanate is added to the filtrate and the mixture is subject to reaction with stirring at room temperature for 16 hours. To the reaction mixture is added methanol and the mixture is stirred for 3 hours to decompose an excessive amount of isocyanate.

The reaction mixture is then charged on a column packed with silica gel having a mesh size of 60–80 and elution is carried out with chloroform. The eluate is concentrated to dryness under reduced pressure to obtain 1.3 g of compound II-9 as a white or light brown amorphus powder.

Figure 18:
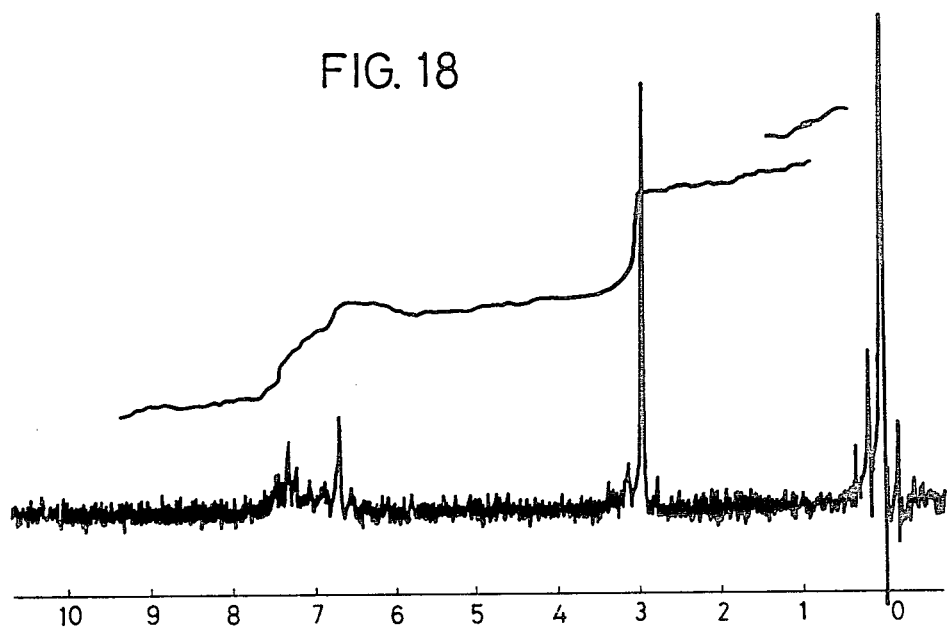

The melting point of the desired product is 143°–145° C. and the infrared spectrum and NMR spectrum are shown in FIGS. 9 and 18, respectively.

EXAMPLE 7

In this example, the same procedures as described in Example 6 are repeated except that the compounds indicted in Table 5 are used instead of phenylisocyanate to obtain the desired compounds shown in Table 5.

TABLE 5

| The desired compound | Isocyanates (g) | Yield (g) | M.P. (°C.) | IR FIG. No. | NMR FIG. No. |
|---|---|---|---|---|---|
| II-4 | hexamethylene diisocyanate (0.8) | 0.61 | 96–99 | 4 | 13 |
| II-5 | tolylene 2,4-diisocyanate (0.9) | 0.79 | 155–157 | 5 | 14 |
| II-6 | m-xylylene diisocyanate (0.9) | 0.59 | 96–100 | 6 | 15 |
| II-7 | 1-naphthylisocyanate (0.8) | 0.84 | 114–117 | 7 | 16 |
| II-8 | acetyl chloride (0.2) | 0.56 | 178–180 | 8 | 17 |

EXAMPLE 8

In this example, 1 g of Bindschedler's Green Leuco Base (Dotite BG, produced by Dojin Yakukagaku Kenkyusho) is dissolved in 20 ml of chloroform. Each of the compounds (isocyanates) indicated in Table 6 is added to the solution and each mixture is subjected to reaction at room temperature for 16 hours. Methanol is added to each reaction mixture to decompose the unreacted isocyanate and the same purification procedures as in Example 6 are repeated to obtain the desired compounds shown in Table 6.

TABLE 6

| Desired compound | Isocyanates | Yield (g) | M.P. (°C.) | IR FIG. No. | NMR FIG. No. |
|---|---|---|---|---|---|
| I-1 | Methyl isothiocyanate | 0.72 | 180–182 | 1 | 11 |
| I-2 | Cyclohexylisocyanate | 0.88 | 133–135 | 2 | 12 |
| I-3 | 3,4-dichloroisocyanate | 1.23 | 207–208 | 3 | — |

EXAMPLE 9

In this example, a procedure similar to that of Example 5 is used except that Meldola Blue is used instead of Methylene Blue to obtain compound II-10 in an oily form.

Figure 19:
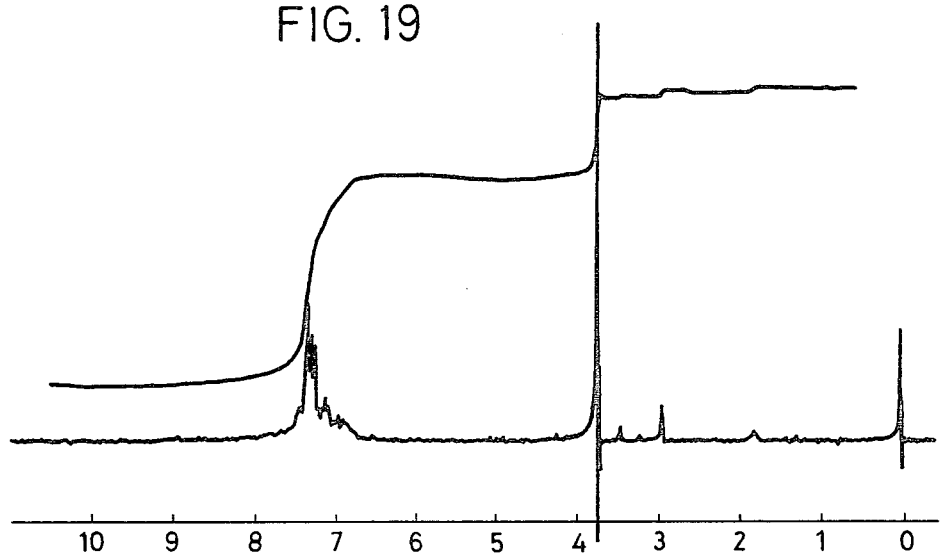

The infrared spectrum and NMR spectrum of the desired compound are shown in FIGS. 10 and 19, respectively.

What is claimed is:

1. A method for the determination of hydrogen peroxide in a sample which comprises reacting the hydrogen peroxide with a chromogen represented by the formulae

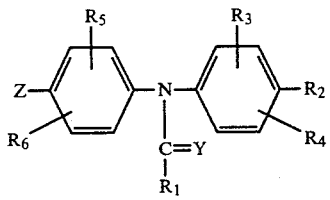

or

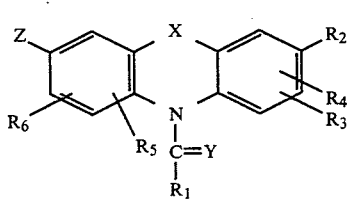

wherein Z represents hydroxyl, amino or substituted amino, Y represents oxygen atom or sulfur atom, $R_1$ represents hydrogen, alkyl, alkenyl, aryl, amino or mono-substituted amino, $R_2$ represents hydrogen, hydroxyl, alkyl, alkenyl, aryl, amino, alkyl-amino or alkoxy, $R_3$, $R_4$, $R_5$ and $R_6$ represent hydrogen, alkyl, alkenyl, acyl, aryl, halogen, sulfo, nitro, carboxyl, hydroxyl, hydroxyalkyl or alkoxy, $R_3$ and $R_4$ or $R_5$ and $R_6$ may form alkenylene, X represents —S—, —O—,

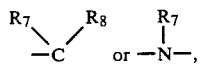

$R_7$ and $R_8$ represent hydrogen, alkyl, alkenyl or aryl, in the presence of peroxidase and measuring the absorbancy of the reaction solution in the visible ray region.

2. A method according to claim 1, wherein Z is a dimethylamino group.

3. A method according to claim 1, wherein $R_2$ is a dimethylamino group.

4. A method according to claim 1, wherein both Z and $R_2$ are dimethylamino group, $R_1$ is a substituted amino group and $R_3$, $R_4$, $R_5$ and $R_6$ are hydrogen.

5. A method according to claim 1, wherein said hydrogen peroxide is a product formed by enzymatic reaction.

6. A method according to claim 5, wherein said enzymatic reaction is the oxidation of a substrate using oxidase.

7. A method according to claim 6, wherein said oxidase is selected from the group consisting of uricase, cholesterol oxidase, xanthin oxidase, choline oxidase, pyruvate oxidase, glycerin-3-phosphate oxidase, acyl Co A oxidase, glycerol oxidase, glucose oxidase and galactose oxidase.

8. A method according to claim 5, wherein said hydrogen peroxide-producing reaction and the reaction of hydrogen peroxide with said chromogen are conducted simultaneously.

9. A method according to claim 1, wherein said reaction is carried out in a buffer solution.

10. A test composition for the guantitative determination of hydrogen peroxide in a sample which comprises a sufficient amount of peroxidase and a chromogen defined in claim 1 to react with said hydrogen peroxide and form a pigment proportional to the amount of hydrogen peroxide in said sample.

11. A test composition according to claim 10 wherein said composition further a contains buffer reagent.

12. A test composition according to claim 10, wherein said composition further contains a member selected from the group consisting of a surfactant, antiseptics and ascorbate oxidase.

13. A test composition according to claim 10, which additionally comprises an enzymatic hydrogen peroxide-producing system in an amount sufficient to produce hydrogen peroxide proportional to the amount of a substrate in said sample.

14. A test composition according to claim 13, wherein said enzymatic hydrogen peroxide-producing system includes an oxidase for said substrate.

* * * * *

UNITED STATES PATENT AND TRADEMARK OFFICE
CERTIFICATE OF CORRECTION

PATENT NO. : 4,384,042
DATED : May 17, 1983
INVENTOR(S) : Akira Miike, et al.

It is certified that error appears in the above-identified patent and that said Letters Patent is hereby corrected as shown below:

Column 6, lines 61 to 66 in the formula, "$R_9R_{10}R$" should be -- $R_9R_{10}N$ --.

Column 12, line 9, "indicted" should be -- indicated --.

Column 14, line 29, "a contains" should be -- contains a --.

Signed and Sealed this

Second Day of August 1983

[SEAL]

Attest:

GERALD J. MOSSINGHOFF

Attesting Officer

Commissioner of Patents and Trademarks